United States Patent
Nomoto et al.

(10) Patent No.: US 8,491,553 B2
(45) Date of Patent: Jul. 23, 2013

(54) INDIVIDUALLY WRAPPED ABSORBENT ARTICLE INCLUDING WRAPPING SHEET

(75) Inventors: Takashi Nomoto, Kagawa (JP); Masashi Uda, Kagawa (JP); Hideaki Morita, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 329 days.

(21) Appl. No.: 12/865,704

(22) PCT Filed: Dec. 17, 2008

(86) PCT No.: PCT/JP2008/072910
§ 371 (c)(1),
(2), (4) Date: Oct. 8, 2010

(87) PCT Pub. No.: WO2009/096109
PCT Pub. Date: Aug. 6, 2009

(65) Prior Publication Data
US 2011/0034897 A1 Feb. 10, 2011

(30) Foreign Application Priority Data
Jan. 30, 2008 (JP) .................... 2008-018494

(51) Int. Cl.
*A61F 13/47* (2006.01)
*A61F 13/551* (2006.01)
*A61F 13/84* (2006.01)

(52) U.S. Cl.
USPC .............................. 604/385.02; 604/385.201

(58) Field of Classification Search
USPC ...................... 604/385.02, 385.201
See application file for complete search history.

(56) References Cited

U.S. PATENT DOCUMENTS 6,186,993 B1 * 2/2001 Toyoshima et al. ...... 604/385.02
6,454,095 B1 * 9/2002 Brisebois et al. ............. 206/494
(Continued)

FOREIGN PATENT DOCUMENTS

EP 1 327 429 7/2003
EP 1 400 223 3/2004
(Continued)

OTHER PUBLICATIONS

International Search Report mailed Mar. 17, 2009 directed to PCT/JP2008/072910; 2 pages.

(Continued)

*Primary Examiner* — Lynne Anderson
*Assistant Examiner* — Kathryn E Ditmer
(74) *Attorney, Agent, or Firm* — Morrison & Foerster LLP (57) ABSTRACT

An individually wrapped absorbent article 1 comprising an absorbent article 2 and a wrapping sheet 3, said absorbent article having a shape being relatively long in a longitudinal direction having a liquid-pervious top-sheet, a liquid-impervious back-sheet and a liquid-retentive absorbent core, on one hand, and said wrapping sheet 3 having a shape being also relatively long in the longitudinal direction arranged to cover the back-sheet of the absorbent article 2, on the other hand, so as to be folded back in the longitudinal direction of the absorbent article 2 by a predetermined fold length dimension L1, respectively, with the top-sheet inside. The wrapping sheet 3 is provided with a first display region 33 having a predetermined length dimension L3 as measured from one end of the wrapping sheet 3 in the longitudinal direction and the length dimension L3 of the first display region 33 is set to be smaller than the fold length dimension L1.

10 Claims, 12 Drawing Sheets

U.S. PATENT DOCUMENTS

| | | | |
|---|---|---|---|
| 6,575,947 B1 * | 6/2003 | Tameishi et al. | 604/385.01 |
| 2003/0065300 A1 | 4/2003 | Suga | |
| 2006/0025739 A1 * | 2/2006 | DiPalma et al. | 604/385.02 |
| 2006/0135927 A1 * | 6/2006 | Zander et al. | 604/385.02 |
| 2006/0137568 A1 * | 6/2006 | MacDonald et al. | 106/31.13 |
| 2007/0073255 A1 * | 3/2007 | Thomas et al. | 604/385.02 |

FOREIGN PATENT DOCUMENTS

| | | |
|---|---|---|
| JP | 5-35124 | 5/1993 |
| JP | 9-58759 | 3/1997 |
| JP | 9-220254 | 8/1997 |
| JP | 2003-93437 | 4/2003 |
| JP | 2003-104441 | 4/2003 |
| JP | 2003-111798 | 4/2003 |
| JP | 2006-180990 | 7/2006 |
| JP | 2007-521117 | 8/2007 |
| WO | WO-99/52484 | 10/1999 |
| WO | WO-2005/065616 | 7/2005 |
| WO | WO-2006/068673 | 6/2006 |
| WO | WO-2009/096109 | 8/2009 |

OTHER PUBLICATIONS

Extended Search Report dated Mar. 27, 2013, directed toward European Application No. 08871838; 6 pages.

* cited by examiner

INDIVIDUALLY WRAPPED ABSORBENT ARTICLE INCLUDING WRAPPING SHEET

REFERENCE TO RELATED APPLICATIONS

This application is a national stage application under 35 USC 371 of International Application No. PCT/JP2008/072910, filed Dec. 17, 2008, which claims the priority of Japanese Application No. 2008-018494, filed Jan. 30, 2008, the contents of which prior applications are incorporated herein by reference.

FIELD OF THE INVENTION

The present invention relates to individually wrapped absorbent articles including a wrapping sheet.

BACKGROUND OF THE INVENTION

Sanitary napkins, one typical example of absorbent articles, are usually dispensed in the form of an individually wrapped sanitary napkin. Such individually wrapped sanitary napkin is adapted to be removed from the wrapping sheet when it is actually used by unsealing the wrapping sheet.

The wrapping sheet which individually wraps the sanitary napkin is often used also to wrap the used sanitary napkin for disposal thereof.

For example, Japanese Patent Application Laid-Open Publication No. 1997-220244 discloses an individually wrapped sanitary napkin with an arrangement such that a rectangular wrapping sheet for the absorbent article is provided on one end thereof with a tape fastener adapted to seal the wrapping sheet containing the absorbent article and to seal the wrapping sheet a second time when it is used to contain the used absorbent article for disposal.

SUMMARY OF THE INVENTION

It should be considered here that exchange of the sanitary napkin is usually carried out within a relatively tight space such as a toilet. Furthermore, when it is desired to wrap the used sanitary napkin again with the wrapping sheet for disposal thereof, it is essential first to position the used sanitary napkin properly on the wrapping sheet so that the used sanitary napkin might not protrude from the wrapping sheet. Then the wrapping sheet on which the used sanitary napkin has been properly positioned must be folded back from one end in the longitudinal direction successively by a given dimension for each folding back. Taking account of such requirements, the wrapping sheet is preferably arranged to facilitate the user to wrap the used sanitary napkin even in a tight space. However, in the individually wrapped absorbent article disclosed in Japanese Patent Application Laid-Open Publication 1997-220254, the wrapping sheet has no ingenuity facilitating the user to wrap the used sanitary absorbent article again with the wrapping sheet for disposal of the used sanitary napkin.

In view of the problem as has been described above, it is a principal object of the present invention to provide an individually wrapped absorbent article inclusive of the wrapping sheet improved so that the wrapping sheet facilitating the used absorbent article to be wrapped again for disposal thereof.

Based on findings that the wrapping sheet may be provided in predetermined regions with displays to achieve the object set forth above, the inventor developed and accomplished the present invention. More specifically, the present invention provides the individually wrapped absorbent article as will be described below.

(1) An individually wrapped absorbent article inclusive of a wrapping sheet comprising an absorbent article having a shape being relatively long in a longitudinal direction having a liquid-pervious top-sheet, a liquid-impervious back-sheet and a liquid-retentive absorbent core and a wrapping sheet having a shape being also relatively long in the longitudinal direction arranged to cover the back-sheet of the absorbent article so as to be folded back in the longitudinal direction of the absorbent article by a predetermined fold length dimension, respectively, with the top-sheet inside, the individually wrapped absorbent article being characterized in that: the wrapping sheet is provided with a first display region having a predetermined length dimension as measured from one end of the wrapping sheet in the longitudinal direction and the length dimension of the first display region is set to be smaller than the fold length dimension.

(2) The individually wrapped absorbent article inclusive of the wrapping sheet described above wherein the first display region is located not to be exposed outside in the individually wrapped absorbent article having been folded back by the fold length dimension.

(3) The individually wrapped absorbent article inclusive of the wrapping sheet described above wherein an end opposite to the one end of the wrapping sheet as viewed in the longitudinal direction is provided with a tape fastener attached thereto and serving to fix the individually wrapped absorbent article in the folded back state.

(4) An individually wrapped absorbent article inclusive of the wrapping sheet comprising an absorbent article having a shape being relatively long in a longitudinal direction having a liquid-pervious top-sheet, a liquid-impervious back-sheet and a liquid-retentive absorbent core, on one hand, and a wrapping sheet having a shape being also relatively long in the longitudinal direction arranged to cover the back-sheet of the absorbent article, on the other hand, so that the individually wrapped absorbent article wherein the individually wrapped absorbent article is folded back onto the top-sheet so that one end in the longitudinal direction may lie inside and the other end lies outside and fixed in the folded shape, the individually wrapped absorbent article being characterized in that: the wrapping sheet is provided with a first display region having a predetermined length dimension as measured from the one end in the longitudinal direction.

(5) The individually wrapped absorbent article inclusive of the wrapping sheet described above wherein the first display region displays information relating to menstruation.

(6) The individually wrapped absorbent article inclusive of the wrapping sheet described above wherein the wrapping sheet is provided with a second display region having a predetermined length dimension as measured from the other end.

(7) The individually wrapped absorbent article inclusive of the wrapping sheet described above wherein the second display region has its length dimension larger than that of the first display region.

(8) The individually wrapped absorbent article inclusive of the wrapping sheet described above wherein the individually wrapped absorbent article folded in three so that the second display region in the wrapping sheet may cover the first display region.

(9) The individually wrapped absorbent article inclusive of the wrapping sheet described above wherein the individually wrapped absorbent article is adapted to be folded in four and the third display region is covered with the second display region in the individually wrapped absorbent article folded in four.

(10) The individually wrapped absorbent article inclusive of the wrapping sheet described above wherein the first display region and the second display region display contents correlated with each other.

(11) The individually wrapped absorbent article inclusive of the wrapping sheet described above wherein the first display region and the third display region display contents correlated to each other.

(12) The individually wrapped absorbent article inclusive of the wrapping sheet described above wherein the tape fastener is formed with a display region associated therewith and the second display region cooperates with the tape fastener's display region to form an integrated graphics.

According to the present invention, the wrapping sheet may be provided in predetermined regions thereof with displays to provide the individually wrapped absorbent article inclusive of the wrapping sheet adapted to wrap the used absorbent article again for disposal thereof.

IDENTIFICATION OF REFERENCE NUMERALS USED IN THE DRAWINGS 1 individually wrapped sanitary napkin (individually wrapped absorbent article inclusive of the wrapping sheet)
2 sanitary napkin (absorbent article)
21 top-sheet
22 main body section
23 wings
24 wings' adhesive regions
25 protection sheet for adhesive regions
26 rear flaps
27 rear flap's adhesive regions
3 wrapping sheet
31 front end section
32 rear end section
33 first display region
34 second display region
35 third display region
4 tape fastener
41 tape fastener's display

DETAILED DESCRIPTION OF THE INVENTION

Now an individually wrapped absorbent article inclusive of a wrapping sheet will be described below on the basis of a preferred first embodiment thereof with reference to the accompanying drawings.

In the first embodiment, the present invention is implemented in the form of an individually wrapped sanitary napkin inclusive of the wrapping sheet.

Figure 1:
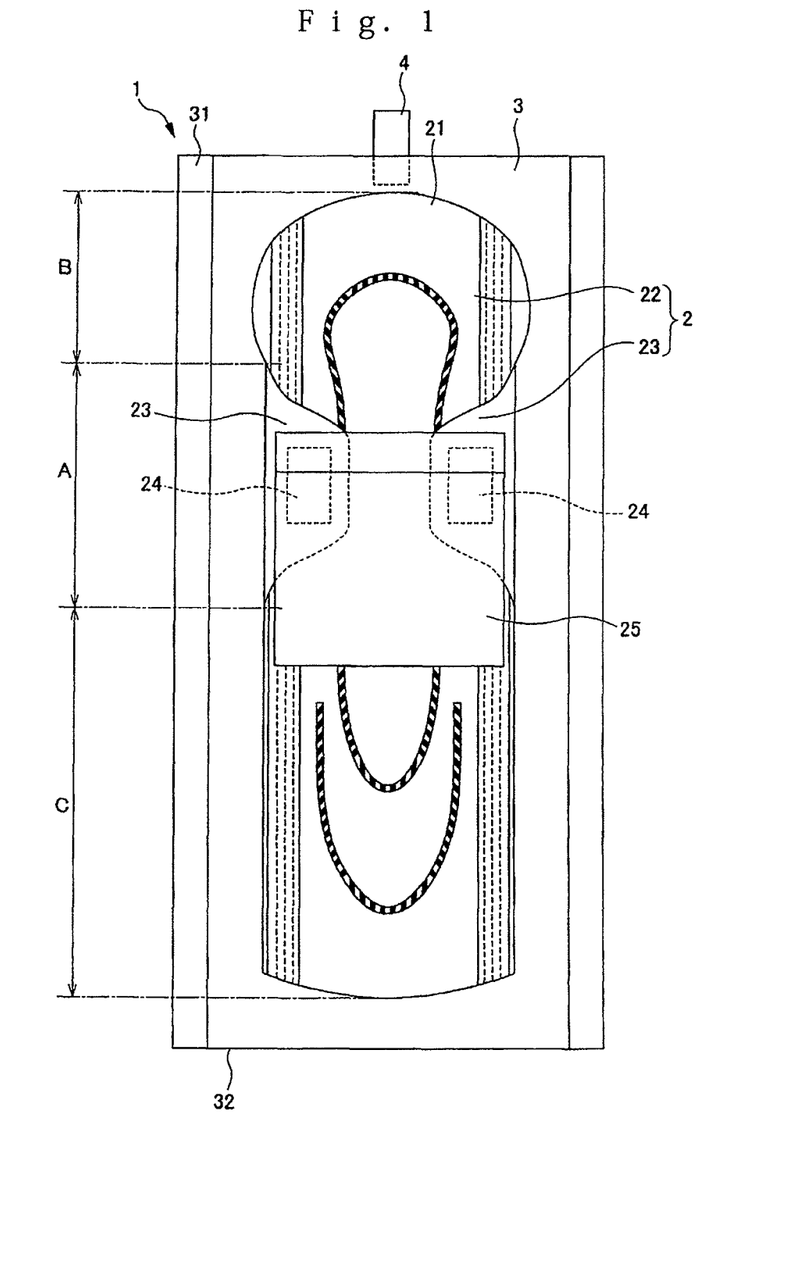
FIG. 1 is a plan view showing an individually wrapped absorbent article (individually wrapped sanitary napkin) according to a first embodiment of the present invention in its unsealed state as viewed from a top-sheet side of the sanitary napkin.
Figure 2:
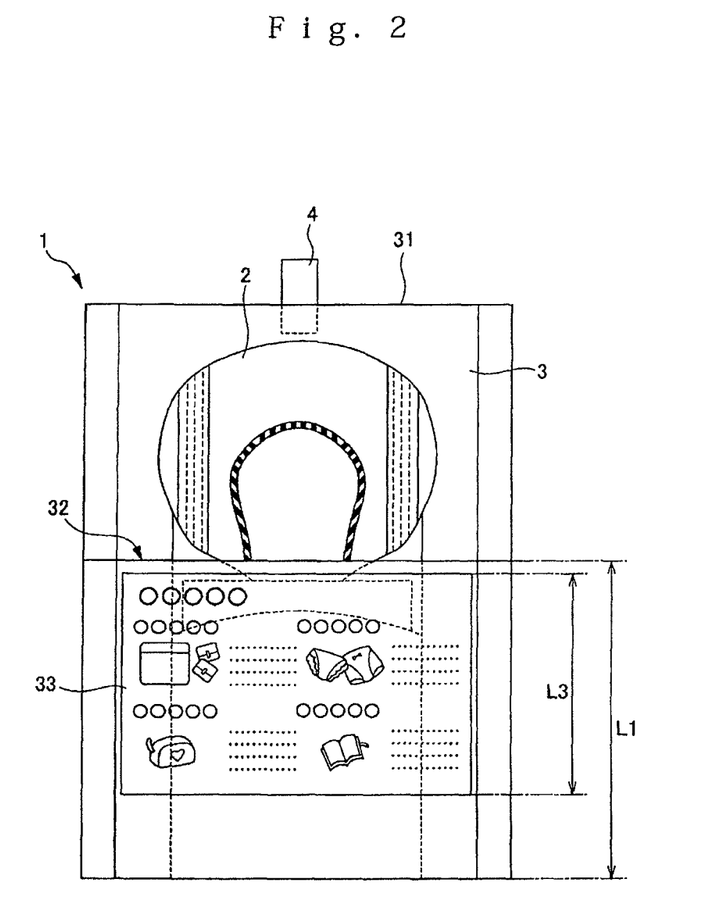
FIG. 2 is a plan view showing the individually wrapped sanitary napkin of FIG. 1 after having been folded back from a rear end side of the wrapped absorbent article by a first folding dimension.
Figure 3:
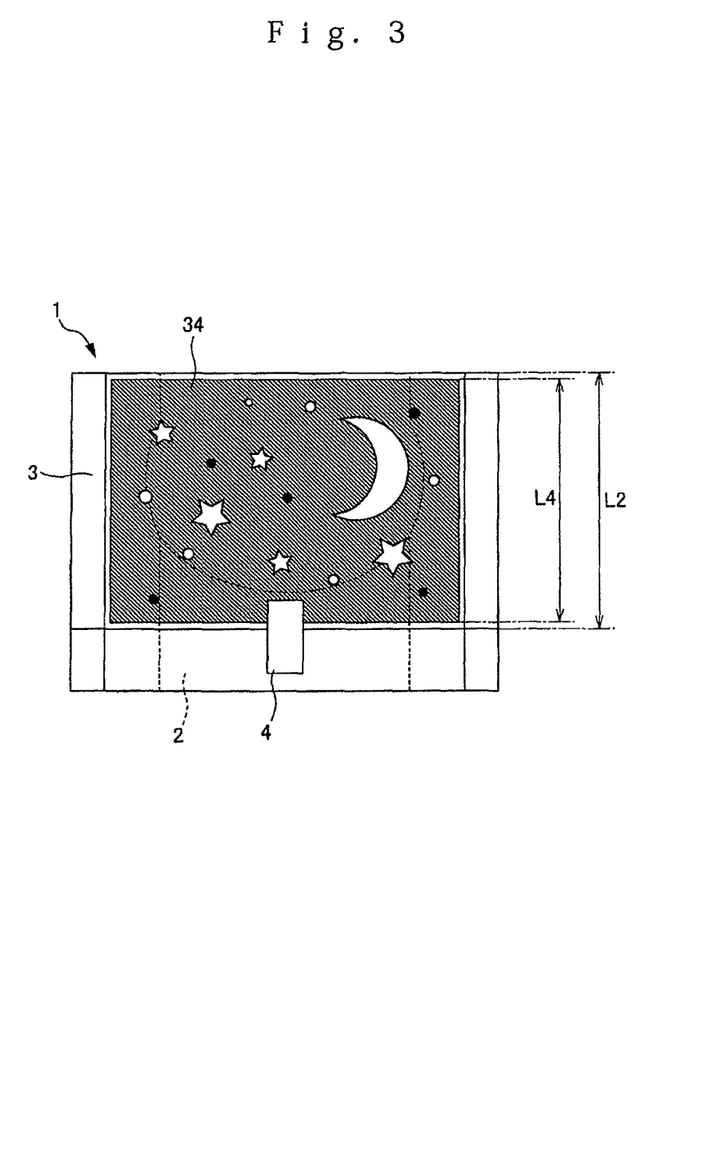
FIG. 3 is a plan view showing the individually wrapped sanitary napkin of FIG. 1 having been folded in three.

Referring to FIGS. 1 through 3, the individually wrapped sanitary napkin 1 comprises a sanitary napkin 2 having a shape which is relatively long in a longitudinal direction and a wrapping sheet 3 having a shape which is also relatively long in the longitudinal direction and located to cover a back-sheet side of the sanitary napkin.

Referring to FIG. 1, the sanitary napkin 2 is shaped to be longer in the longitudinal direction and has a section A adapted to face the relevant excretion organ of the wearer when the sanitary napkin 2 is put on, a front section B at a distance from the section A toward the wearer's ventral side when the sanitary napkin 2 is put on and a rear section C at a distance from the section A toward the wearer' dorsal side when the sanitary napkin 1 is put on.

The sanitary napkin 2 comprises a liquid-pervious top-sheet 21 on the side facing the wearer's skin, a liquid-impervious back-sheet (not shown) on the side facing away from the wearer's skin and a liquid-retentive absorbent core (not shown) sandwiched between the top-sheet 21 and the back-sheet. The sanitary napkin 2 has a main body 22 shaped to be relatively long in the longitudinal direction and a pair of wings 23, 23 extending outward in the transverse direction of both side edges of the main body 22.

The main body 22 is provided on its side facing away from the wearer's skin with main body's adhesive regions (not shown) extending in the longitudinal direction and the respective wings 23, 23 are provided on the side thereof facing away from the wearer's skin (i.e., on the back-sheet side) with wings' adhesive regions 24, 24, respectively.

The sanitary napkin 2 having a pair of the wings 23, 23 folded back onto the top-sheet 21 is placed on the wrapping sheet 3 so that the main body's adhesive regions may be temporarily bonded to the wrapping sheet 3. The wings' adhesive regions 24, 24 provided on the respective wings 23, 23 are covered with a protecting sheet 25.

A front end portion of the adhesive region protecting sheet 25 is folded back and bonded to a rear end portion 32 of the wrapping sheet 3 by means of adhesive (not shown) when the individually wrapped sanitary napkin 1 is folded back.

Referring to FIG. 1, the wrapping sheet 3 has a substantially rectangular shape and provided on a front end 31 as one of its longitudinally opposite ends with a tape fastener 4. The wrapping sheet 3 has a length dimension larger than that of the sanitary napkin 2 and a width dimension larger than that of the main body 22 of the sanitary napkin 2. In other words, the wrapping sheet 3 is formed to be one size larger than the main body 22 of the sanitary napkin 2. The wrapping sheet 3 is formed by transparent or translucent non-woven fabric or plastic film and has its inner surface treated with release agent. The sanitary napkin 2 is positioned so that the main body's adhesive region may be releasably stuck to the inner surface of the wrapping sheet 3.

Figure 4:
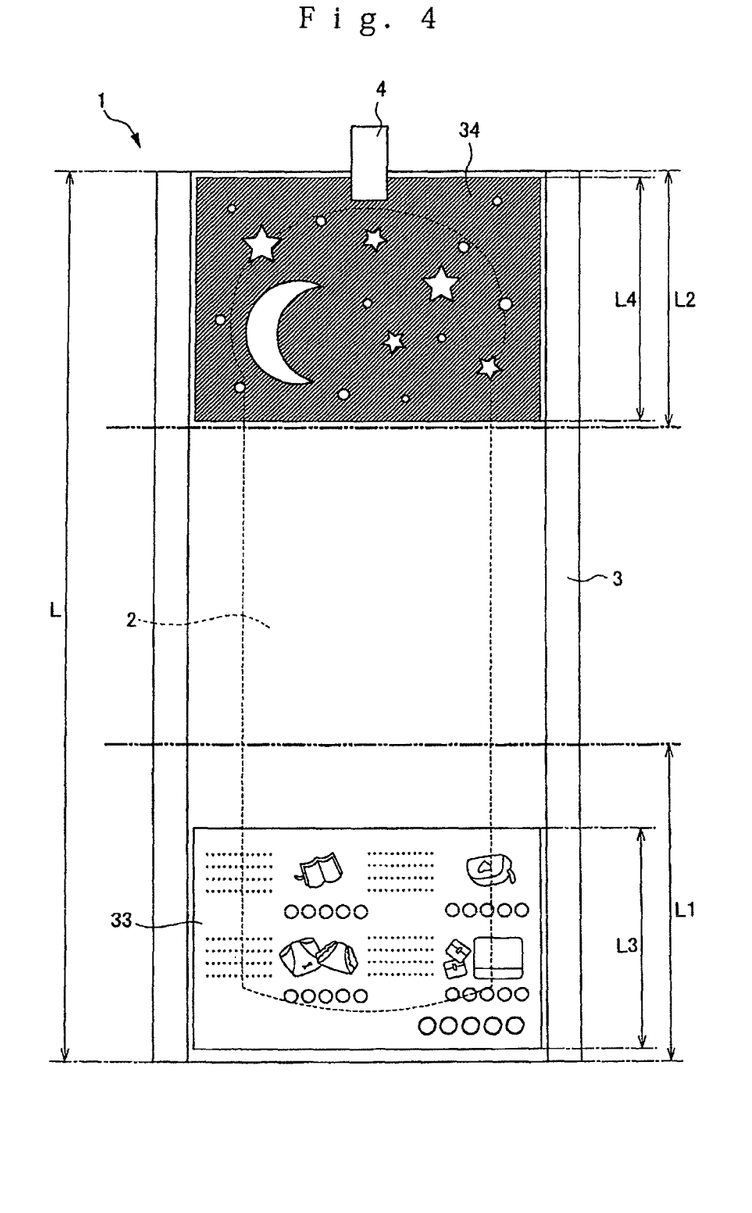
FIG. 4 is a plan view showing the individually wrapped sanitary napkin of FIG. 1 as viewed from the outer surface of the wrapping sheet.

Referring to FIGS. 2 and 4, the wrapping sheet 3 is provided on its outer surface with a first display region 33 in a range extending from the rear end 32 opposite to the front end 31 by a predetermined dimension. As will be apparent from FIG. 4, a length dimension L3 of the first display region 33 is smaller than a first fold length dimension L1 which will be described later.

The wrapping sheet 3 is further provided on its outer surface, as will be apparent from FIGS. 3 and 4, with a second display region 34 in a range extending from the front end 31 of the wrapping sheet 3 by a predetermined dimension. A length dimension L4 of the second display region 34 is larger than the length dimension L3 of the first display region 33. The length dimension L4 of the second display region 34 is substantially same as a second fold length dimension L2 as will be described later.

The first display region 33 displays information (characters and graphics) relating to menstruation as seen in FIGS. 2 and 4 the second display region 34 provides graphics quite unconnected with the sanitary article as will be seen in FIGS. 3 and 4. According to the first embodiment, the second display region 34 provides graphics such as moon and stars in deep colored night sky.

While the first display region 33 as well as the second display region 34 has been described hereinabove to be provided on the outer surface of the wrapping sheet 3, these display regions 33, 34 can be visually recognized from the inner surface since the wrapping sheet 3 is transparent or translucent. The second display region 34 is deep colored and therefore the wrapping sheet 3 has no transparency in the second display region 34.

Referring to FIG. 1, the sanitary napkin 2 is positioned with respect to the inner surface of the wrapping sheet 3 so that the front section B of the sanitary napkin 2 lies on the side of the front end side 31 of the wrapping sheet 3 and the rear section C of the sanitary napkin 2 lies on the side of the rear end 32 of the wrapping sheet 3.

The individually wrapped sanitary napkin 1 is adapted to be folded back on itself so that one end of an assembly of the wrapping sheet 3 and the sanitary napkin 2 wrapped therewith as viewed in the longitudinal direction lies inside and the other end lies outside. The individually wrapped sanitary napkin 1 folded back on itself in this manner is fixed in such folded back configuration by the tape fastener 4.

According to the first embodiment, with the front section B of the sanitary napkin 2 positioned on the front end 31 of the wrapping sheet 3 and the rear section C of the sanitary napkin 2 positioned on the side of the rear end 32 of the wrapping sheet 3, the sanitary napkin 2 and the wrapping sheet 3 are folded together from the rear section C and the rear end 32, respectively, onto the top-sheet 21 by the predetermined first fold length dimension L1 and then folded together from the front section B and the front end 31, respectively, onto the top-sheet 21. In this manner, the assembly of the sanitary napkin 2 and the wrapping sheet 3 is folded in three. Then, the assembly is fixed by the tape fastener 4 in this state folded in three. It should be understood that transversely opposite side edges of the wrapping sheet 3 folded in three are heat sealed.

The first fold length dimension L1 is in a range of 30 to 40% of a length L of the wrapping sheet 3 in the longitudinal direction. The second fold length dimension L2 is smaller than the first fold length dimension L1 and specifically in a range of less than 20 to 30% of the length L of the wrapping sheet 3 in the longitudinal direction.

The individually wrapped sanitary napkin 1 according to the first embodiment is folded so that the rear end 32 of the wrapping sheet 3 lies inside and the front end 31 thereof lies outside. In the individually wrapped sanitary napkin 1 folded in this manner, the second display region 34 is exposed on the outer side thereof and the first display region 33 is covered with this second display region 34 and the front section B of the sanitary napkin 2. In other words, the first display region 33 is positioned so as to be not exposed outside of the individually wrapped sanitary napkin 1 in its folded state.

With the individually wrapped sanitary napkin 1 folded in this manner, the second display region 34 having graphics which are quite not suggestive of the sanitary article is exposed outside and advantageously makes it difficult the wrapped article to be recognized as the sanitary napkin by its appearance.

When it is desired to use the individually wrapped sanitary napkin 1 according to the first embodiment, the tape fastener 4 is peeled off to unseal the front end 31 of the wrapping sheet 3 and the side of the front section B of the sanitary napkin 2 outward (See FIG. 2). In this phase, the first display region 33 which has been covered with the second display region 34 in the folded state is exposed outside. The first display region 33 containing the information relating to menstruation is useful to reinforce the user's knowledge and/or to enlighten the right pieces of information on menstruation. The first display region 33 adapted to display the information relating to menstruation is suitable particularly in the individually wrapped sanitary napkin 1 for teenaged wearer having her first period for whom it is essential to have right knowledge and information relating to menstruation.

In the folded state prior to actual use of the sanitary napkin 2, the first display region 33 is covered with the second display region 34 and not exposed outside and therefore the display of the information relating to menstruation is not visually recognized.

In the case of the individually wrapped sanitary napkin 1 according to the first embodiment, after the front end 31 of the wrapping sheet 3 and the front section B of the sanitary napkin 2 have been unsealed outward, these front end 31 and front section B are respectively pinched with the fingers and peeled off from each other to separate the wrapping sheet 3 and the sanitary napkin 2 from each other. The protecting sheet 25 for adhesive regions bonded to the rear end 32 of the wrapping sheet 3 is separated together with the wrapping sheet 3 from the sanitary napkin 2 as the wrapping sheet 3 and the sanitary napkin 2 are separated from each other. In this way, the wearer may use the sanitary napkin 2 having been separated from the wrapping sheet 3.

The wrapping sheet 3 having served to wrap the sanitary napkin 2 until the latter is actually used by the wearer may be used also to wrap the used sanitary napkin 32. Specifically, in view of the fact that the used sanitary napkin is inevitably stained with menstrual blood, the used sanitary napkin 2 may be wrapped again with the wrapping sheet 3 and thereby disposed in a sanitary manner.

Figure 5:
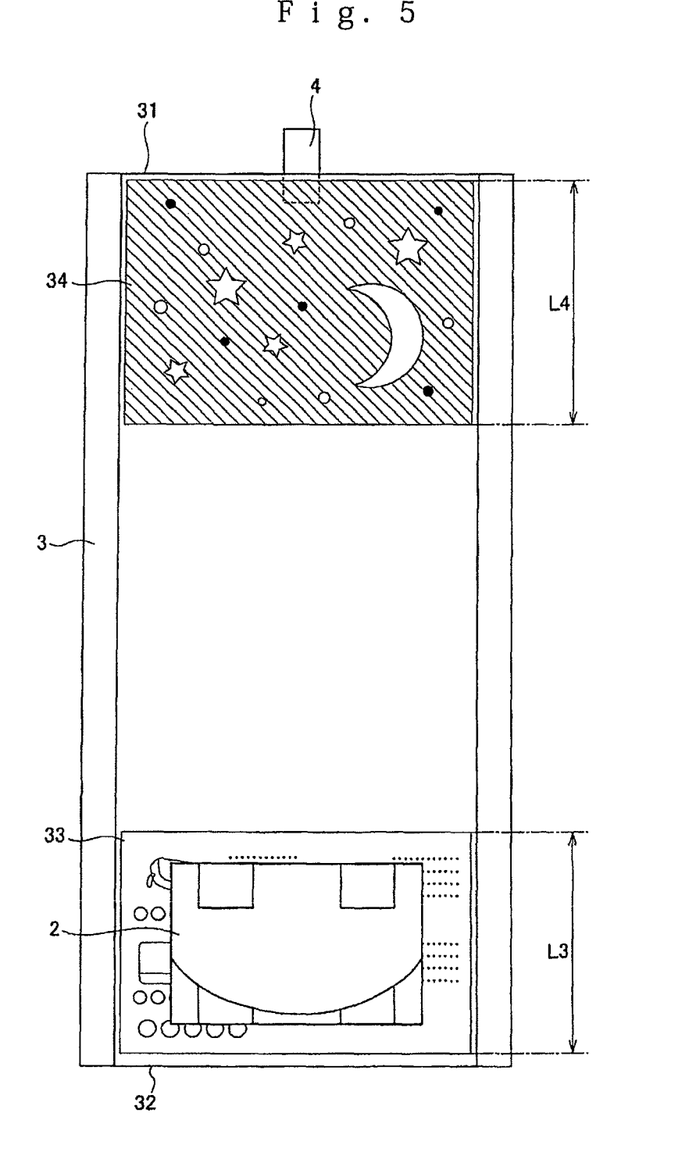
FIG. 5 is a plan view illustrating a step of positioning the used sanitary napkin so as to overlap a first display region of the wrapping sheet in the course of wrapping the used sanitary napkin with the wrapping sheet.
Figure 6:
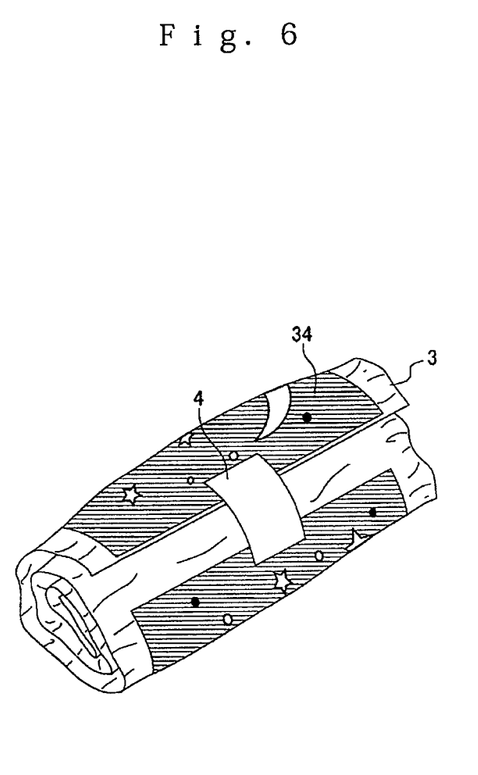
FIG. 6 is a diagram illustrating the used sanitary napkin completely wrapped around with the wrapping sheet.

Specifically, the wrapping sheet 3 may be laid on the outer surface of the back-sheet in the used sanitary napkin 2 (See FIG. 5) and then the wrapping sheet 3 may be folded back in the longitudinal direction to wrap around the used sanitary napkin 2 with the wrapping sheet 3 (See FIG. 6).

For disposal of the used sanitary napkin 2, the used sanitary napkin 2 is placed on the wrapping sheet 3 preferably in the vicinity of the rear end 32 provided not with the tape fastener 4. This is for the reason that the used sanitary napkin 2 may be folded back together with the wrapping sheet 3 from the side of the rear end 32 of the wrapper sheet 3 and the completely wrapped and folded used sanitary napkin 2 may be easily fixed by the tape fastener 4 provided on the front end 31 of the wrapping sheet 3.

The wrapping sheet 3 in the individually wrapped sanitary napkin 1 according to the first embodiment is provided in the range defined by the predetermined length dimension from the rear end 32 with the first display region 33. This first display region 33 may be used as an indicator when the used sanitary napkin 2 is positioned on the wrapping sheet 3. The wrapping sheet 3 is sufficiently transparent or translucent to facilitate the first display region 33 to be visually recognized from the inside (See FIG. 5).

The first display region 33 may be used as an indicator suggesting the proper fold length dimension by which the wrapping sheet may be folded back together with the used sanitary napkin 2 positioned thereon in the longitudinal direction for disposal of the used sanitary napkin 2. More specifically, referring to FIG. 5, after the used sanitary napkin 2 is placed just on the first display region 33 of the inner surface of the wrapping sheet 3, the wrapping sheet 3 may be folded back by the length dimension L3 of the first display region 33 to facilitate the used sanitary napkin 2 to be wrapped around with the wrapping sheet 3 and thereby to be disposed in a sanitary manner.

When the wrapping sheet 3 is successively folded back by the length dimension of the first display region 33, respectively, in the longitudinal direction after the used sanitary napkin 2 has been placed just on the first display region 33 of the inner surface of the wrapping sheet 3, the outer surface of the used sanitary napkin 2 successively folded back is covered with the second display region 34 provided in the vicinity of the front end 31 of the wrapping sheet 3 (See FIG. 6). The second display region 34 is deep colored and has no transparency and in consequence, the used sanitary napkin 2 covered with the second display region 34 is not visually recognized. In this way, the feeling experienced by the user at the moment of disposal of the used sanitary napkin is noticeably improved.

The second display region 34 is dimensioned to have a length larger than the length of the first display region 33 so that, after the used sanitary napkin 2 has been successively folded back by the length dimension of the first display region 33, respectively, the second display region 34 can cover the substantially entire outer surface of the used sanitary napkin 2 folded back in this manner for disposal thereof.

The sanitary napkin 2 constituting the individually wrapped sanitary napkin 1 according to the first embodiment is not limited to the particular one as has been exemplarily described above but the other conventional type of sanitary napkin 2 also may be used. The kinds of material for component members of the sanitary napkin 2 such as the top-sheet 21, the back-sheet and the absorbent core also may be selected from the various kinds of material usually used in the relevant technical field.

Now a second embodiment of the individually wrapped sanitary napkin according to the present invention will be described in reference with the FIGS. 7 through 10. Aspects of the second embodiment distinguished from those of the first embodiment will be preliminarily described hereinafter and the members same as or similar to those in the first embodiment are designated with same or similar reference numerals. It should be understood that the description of the first embodiment is applicable to the second embodiment unless otherwise specified.

In the case of the individually wrapped sanitary napkin 1 according to the second embodiment, the sanitary napkin 2 are folded back together with the wrapping sheet 3 in four in the longitudinal direction as will be apparent from FIGS. 7 through 10.

Figure 7:
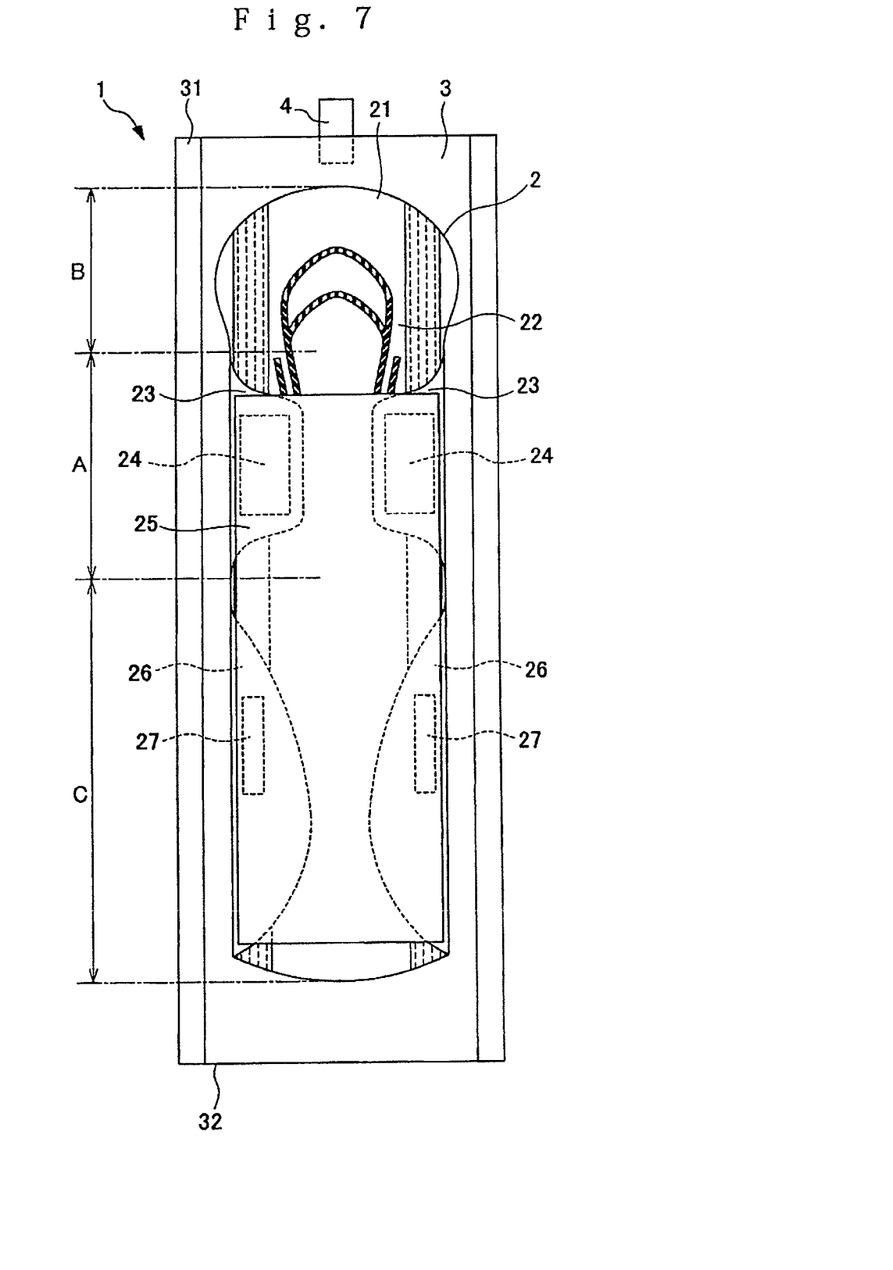
FIG. 7 a plan view showing the individually wrapped absorbent article (individually wrapped sanitary napkin) according to a second embodiment of the present invention in its unsealed state as viewed from a top-sheet side of the sanitary napkin.

Referring to FIG. 7, the sanitary napkin 2 according to the second embodiment is dimensioned to be longer than the sanitary napkin 2 according to the first embodiment and the rear section C is provided with a pair of rear flaps 26, 26. These rear flaps 26, 26 are provided on the surfaces thereof facing away from the wearer's skin (i.e., on the side of the back-sheet) with rear flaps' adhesive regions 27, 27, respectively.

Referring to FIG. 7, the sanitary napkin 2 having a pair of the wings 23, and a pair of the rear wings 26, 26 folded back on the top-sheet 21 is placed on the wrapping sheet 3 so that the main body's adhesive regions may be temporarily bonded to the wrapping sheet 3. The wings' adhesive regions 24, 24 in a pair of the wings 23, 23 and the rear wings' adhesive regions 27, 27 in a pair of the rear flaps 26, 26 are covered with the adhesive region protecting sheet 25.

The adhesive region protecting sheet 25 is bonded in its longitudinally middle region to the rear end 32 of the wrapping sheet 3 by means of adhesive (not shown) as the individually wrapped sanitary napkin 1 is folded back.

Figure 8:
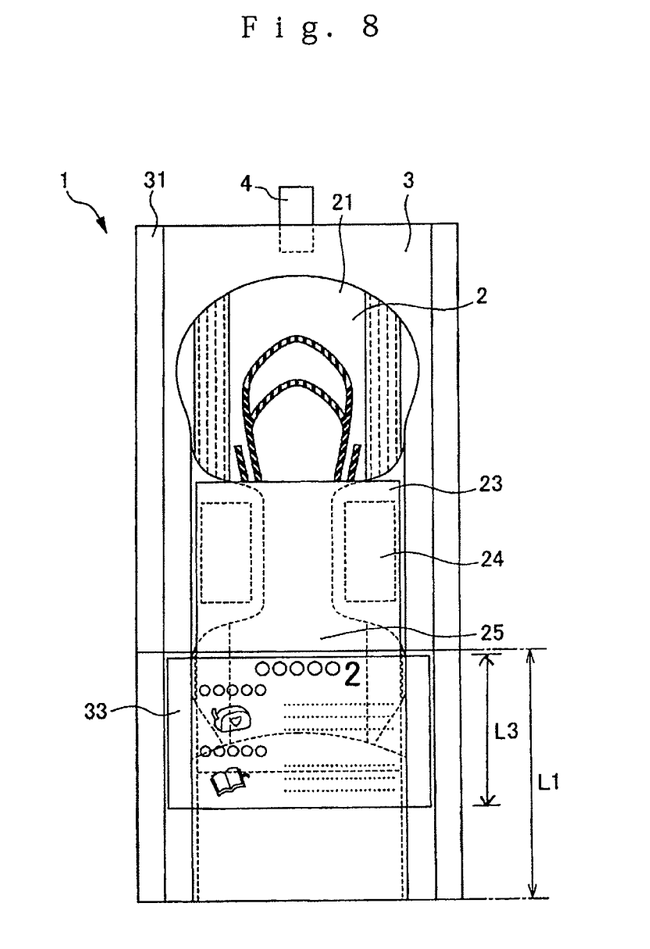
FIG. 8 is a plan view showing the individually wrapped sanitary napkin of FIG. 7 after having been folded back from the rear end side of the wrapped absorbent article by the first folding dimension.
Figure 9:
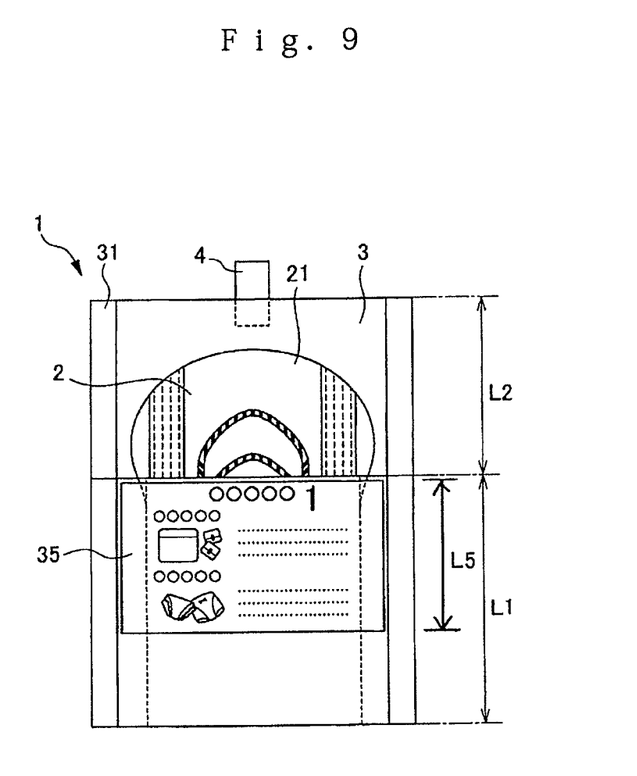
FIG. 9 is a plan view showing the individually wrapped sanitary napkin of FIG. 8 after having been further folded back from the rear end side of the wrapped absorbent article by the first folding dimension.
Figure 10:
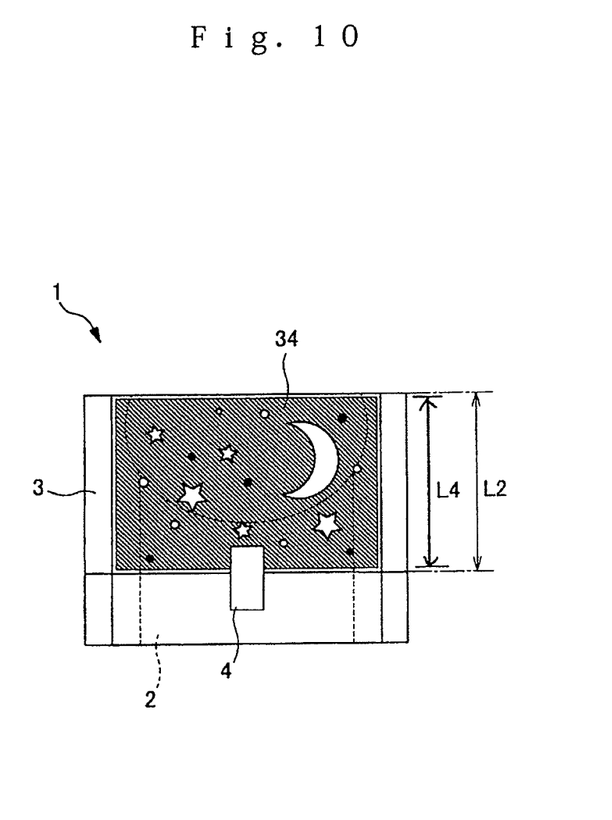
FIG. 10 is a plan view showing the individually wrapped sanitary napkin of FIG. 7 having been folded in three.

In the case of the individually wrapped sanitary napkin 1 according to the second embodiment, the wrapping sheet 3 and the sanitary napkin 2 placed on the inner surface of the wrapping sheet are first folded back together, as illustrated by FIG. 8, from side of the rear section C of the sanitary napkin 2 and the side of the rear end 32 of the wrapping sheet 3 onto the top-sheet 21 of the sanitary napkin 2 by the first fold length dimension L1. Then, the wrapping sheet 3 and the sanitary napkin 2 are folded back again, as illustrated by FIG. 9, from the side of the ear section C of the sanitary napkin 2 and the side of the rear end 2 of the wrapping sheet 3 by a length dimension substantially same as the first fold length dimension L1. Finally, the wrapping sheet 3 and the sanitary napkin 2 are folded back, as illustrated by FIG. 10, from the side of the front section B of the sanitary napkin 2 and the side of the front end 31 of the wrapping sheet 3 by a second fold length dimension L2. In this manner, the sanitary napkin 2 and the wrapping sheet 3 are folded together in four.

The individually wrapped sanitary napkin 1 according to the second embodiment is provided with a third display region 35 adapted to be covered with the second display region 34 when the individually wrapped sanitary napkin 1 is folded back in the manner as has been described just above. A length dimension L5 of the third display region 35 is set to be substantially same as the length dimension L3 of the first display region 33 and smaller than the length dimension L4 of the second display region 34 as well as the first fold length L1. According to the second embodiment, the third display region 35 displays information relating to menstruation.

When it is desired to use the individually wrapped sanitary napkin 1 according to the second embodiment, first the tape fastener 4 is peeled off to unseal the front end 31 of the wrapping sheet 3 and the front section B of the sanitary napkin 2 outward (See FIG. 9). Upon unsealing, the third display region 35 having been covered with the second display region 34 is exposed outside. The third display region 35 also displays information relating to menstruation and serves to reinforce the wearer's knowledge and/or to enlighten the right pieces of information on menstruation.

In folded state prior to actual use of the sanitary napkin 2, the third display region 35 is covered with the second display region 34 not to be exposed outside and consequently the display of information relating to menstruation is not visually recognized.

In the case of the individually wrapped sanitary napkin 1 according to the second embodiment, after the front end 31 of the wrapping sheet 3 and the front section B of the sanitary napkin 2 have been unsealed outward, the wrapping sheet 3 and the sanitary napkin 2 are further unsealed, in the third display region 35, toward the rear end 32 of the wrapping sheet 3 (See FIG. 8). In this state, the first display region 33 is exposed outside. According to the second embodiment, the first display region 33 also displays information relating to menstruation.

Upon unsealing the individually wrapped sanitary napkin 1, the wearer of the sanitary napkin 2 first visually recognizes information displayed in the third display region 35 and then visually recognizes information displayed in the first display region 33. The third display region 35 and the first display region 33 display pieces of information correlated to each other and thereby allow the wearer of the sanitary napkin 2 to learn a good deal of knowledge on menstruation and, in addition, to take an interest in unsealing the individually wrapped sanitary napkin 1.

In the case of the individually wrapped sanitary napkin 1 according to the second embodiment, with the first display region 33 exposed on the outer surface, the front end 31 of the wrapping sheet 3 and front section B of the sanitary napkin 2 are respectively pinched with the fingers and peeled off from each other to separate the wrapping sheet 3 and the sanitary napkin 2 from each other. The protecting sheet 25 for adhesive regions bonded to the rear end 32 of the wrapping sheet 3 is separated together with the wrapping sheet 3 from the sanitary napkin 2 as the wrapping sheet 3 and the sanitary napkin 2 are separated from each other. In this way, the wearer may use the sanitary napkin 2 having been separated from the wrapping sheet 3.

The individually wrapped sanitary napkin 1 according to the second embodiment achieves the same effect as achieved by the first embodiment and further provides additional pieces of information relating to menstruation by the third display region 35.

It should be appreciated here that the present invention is not limited to the heretofore described embodiments and these embodiments may be varied or modified in many ways without departing from scope and spirit of the present invention.

For example, while the first display region 33 is adapted to display the information relating to menstruation according to the first embodiment, the content to be displayed in the first display region 33 is not limited to such category of information.

It is possible for the first and second display regions 33, 34 to display respective contents correlated with each other. For example, the second display region 34 may display illustration of Christmas tree, on one hand, and the first display region 33 may display characters or graphics correlated with Christmas Day, on the other hand, as illustrated by FIGS. 11 and 12.

The first display region 33 and the second display region 34 may display the contents correlated with each other to give the wearer a certain pleasure or interest in unsealing the individually wrapped sanitary napkin 1.

Figure 11:
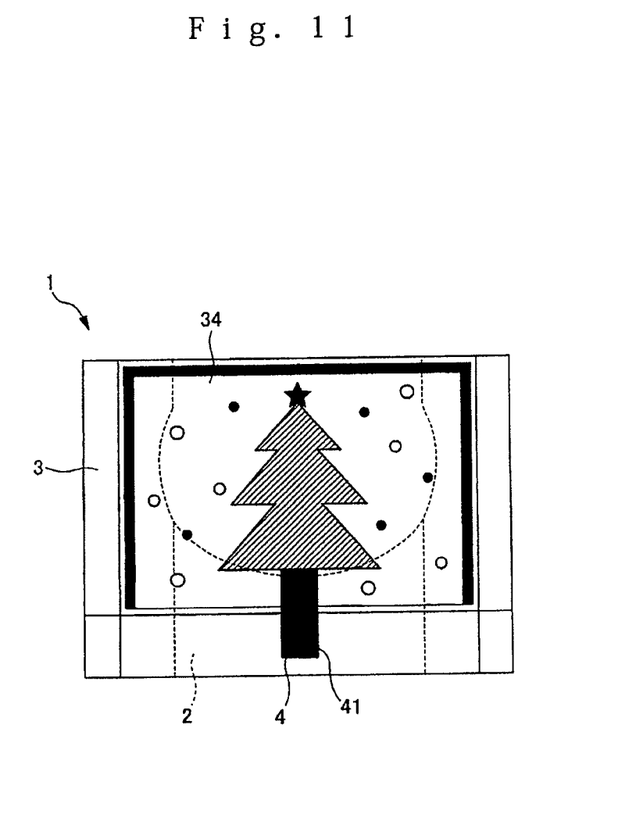
FIG. 11 is a diagram illustrating another embodiment of a second display region on the wrapping sheet in the individually wrapped sanitary napkin according to the present invention.
Figure 12:
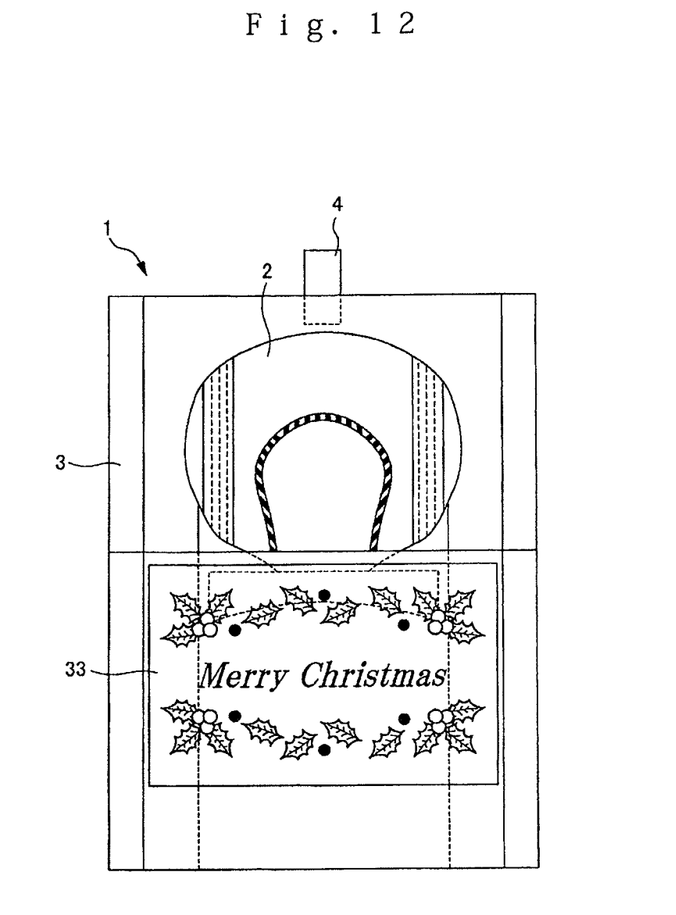
FIG. 12 is a diagram illustrating another embodiment of the first display region on the wrapping sheet in the individually wrapped sanitary napkin according to the present invention.

In addition, the tape fastener 4 is provided with a display region 41 exclusively associated with the tape fastener 4 as will be apparent from FIG. 11. It is possible to form an integrated graphics by combining the content displayed in the second display region 34 with the content displayed in the tape fastener's display region 41.

While the wrapping sheet is formed by transparent or translucent non-woven fabric or plastic film and one surface thereof is release agent treated according to the first and second embodiments, the wrapping sheet 3 formed by transparent or translucent non-woven fabric or plastic film may be provided on its inner surface with a separate sheet member such as release paper. In this case, the separate sheet member such as release paper will be coated on its inner surface with release agent.

In this case, it is also possible to provide the first display region 33, the second display region 34 and the third display region 35 on the outer surface of the sheet member. The non-woven fabric or the plastic film provided on the outer surface of the sheet member is transparent or translucent and therefore the sanitary napkin wearer can visually recognize the first display region 33, the second display region 34 and the third display region 35 even when these display regions 33, 34, are provided on the outer surface of the sheet member.

The absorbent article as one component of the individually wrapped absorbent article according to the present invention is not limited to the sanitary napkin but may be implemented in the form of incontinent pad, panty-liner, disposable diaper or the like

The invention claimed is:

1. An individually wrapped absorbent article comprising an absorbent article and a wrapping sheet, said absorbent article having a shape being relatively long in a longitudinal direction having a liquid-pervious top-sheet, a liquid-impervious back-sheet and a liquid-retentive absorbent core and said wrapping sheet having a shape being also relatively long in the longitudinal direction arranged to cover said back-sheet of said absorbent article so as to be folded back in the longitudinal direction of said absorbent article by a predetermined fold length dimension with said top-sheet inside, wherein said individually wrapped absorbent article is folded back onto said top-sheet so that one end in the longitudinal direction lies inside and the other end lies outside and fixed in the folded shape;

said other end of said wrapping sheet is provided with a tape fastener attached thereto to fix said individually wrapped absorbent article in the folded back shape, said wrapping sheet comprising a first display region having a predetermined length dimension as measured from said one end of said wrapping sheet in the longitudinal direction, wherein the predetermined length dimension of said first display region is smaller than said predetermined fold length dimension of said wrapping sheet;

said wrapping sheet is provided with a second display region having a predetermined length dimension as measured from said other end;

said wrapping sheet in said second display region has no transparency, and said wrapping sheet except said second display region is transparent or translucent; and said second display region has said length dimension larger than that of said first display region, wherein said wrapping sheet is folded such that said second display region of said wrapping sheet covers said first display region of said wrapping sheet.

2. The individually wrapped absorbent article according to claim 1, wherein said first display region is folded back by said fold length dimension to avoid seeing said first display region outside of said individually wrapped absorbent article.

3. The individually wrapped absorbent article according to claim 1, wherein said first display region and said second display region display contents correlated with each other.

4. The individually wrapped absorbent article according to claim 1, wherein said first display region displays information relating to menstruation.

5. The individually wrapped absorbent article according to claim 4, wherein said second display region displays graphics unrelated to menstruation.

6. The individually wrapped absorbent article according to claim 1, wherein said individually wrapped absorbent article is folded in three so that said second display region in said wrapping sheet covers the first display region.

7. The individually wrapped absorbent article according to claim 1, wherein said individually wrapped absorbent article is adapted to be folded in four, and said wrapping sheet includes a third display region being covered with said second display region in said individually wrapped absorbent article folded in four.

8. The individually wrapped absorbent article according to claim 7, wherein said first display region and said third display region display contents correlate to each other.

9. The individually wrapped absorbent article according to claim 1, wherein said tape fastener is formed with a display region associated therewith and said second display region cooperates with said tape fastener's display region to form an integrated graphic.

10. The individually wrapped absorbent article according to claim 1, wherein said wrapping sheet has an inner surface which is the side facing said absorbent article when wrapping said absorbent article and an outer surface opposite to said inner surface, and said first and second display regions are on said outer surface of said wrapping sheet and are visually recognized from a side of said inner surface.

\* \* \* \* \*